United States Patent

Carlsson et al.

[11] Patent Number: 5,851,115
[45] Date of Patent: Dec. 22, 1998

[54] METHOD AND ARRANGEMENT FOR COLLECTING DATA FOR PRODUCTION OF REPLACEMENT DENTAL PARTS FOR THE HUMAN BODY

[75] Inventors: Lennart Carlsson, Molndal; Anders Lie, Bohus, both of Sweden

[73] Assignee: Nobel Biocare AB, Gohenborg, Sweden

[21] Appl. No.: 495,620

[22] PCT Filed: Nov. 29, 1994

[86] PCT No.: PCT/SE94/01142

§ 371 Date: Dec. 5, 1995

§ 102(e) Date: Dec. 5, 1995

[87] PCT Pub. No.: WO95/15731

PCT Pub. Date: Jun. 15, 1995

[30] Foreign Application Priority Data

Dec. 6, 1993 [SE] Sweden .................................. 9304042

[51] Int. Cl.[6] .................................................. A61C 5/00
[52] U.S. Cl. .......................................... 433/215; 433/223
[58] Field of Search ..................... 433/215, 223; 396/324

[56] References Cited

U.S. PATENT DOCUMENTS

| | | |
|---|---|---|
| 2,771,013 | 11/1956 | Mast ........................................ 396/324 |
| 4,575,805 | 3/1986 | Moermann et al. ..................... 433/223 |
| 5,320,462 | 6/1994 | Johansson et al. ....................... 409/84 |
| 5,372,502 | 12/1994 | Massen et al. .......................... 433/215 |
| 5,384,862 | 1/1995 | Echerer et al. ............................. 382/6 |
| 5,401,170 | 3/1995 | Nonomura ............................... 433/223 |
| 5,604,817 | 2/1997 | Massen et al. .......................... 433/215 |

FOREIGN PATENT DOCUMENTS

| | | |
|---|---|---|
| 0490848 | 6/1992 | European Pat. Off. . |
| 0541500 | 5/1993 | European Pat. Off. . |
| WO 90/14803 | 12/1990 | WIPO . |

Primary Examiner—John J. Wilson
Attorney, Agent, or Firm—Law Offices Pollock, Vande Sande & Priddy

[57] ABSTRACT

A method and apparatus thereof for collecting control data for the production of replacement dental parts. The method includes the steps of imaging a body area and a replacement part with a single imaging device which is arranged to take a simultaneous picture of the body area from different angles during one exposure. The pictures are developed and scanned with a reading device which generates digitized data of the imaged body area and the replacement part to be applied in that area. The digitized data is transmitted to computer equipment which automatically reproduces the body area and replacement part on a screen. A computer program calculates spacial relations data of surfaces of the body area and replacement part and the data is used as control data in making and fitting the replacement part in the human body.

11 Claims, 3 Drawing Sheets

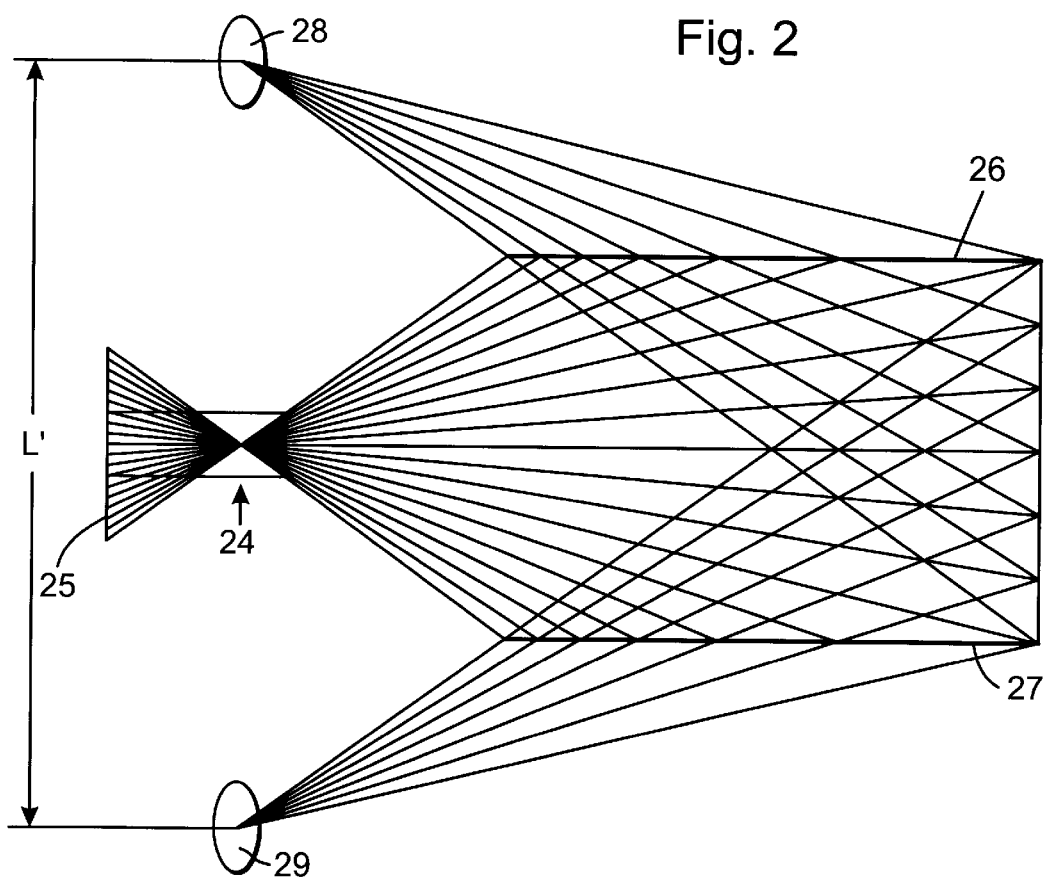
Fig. 2
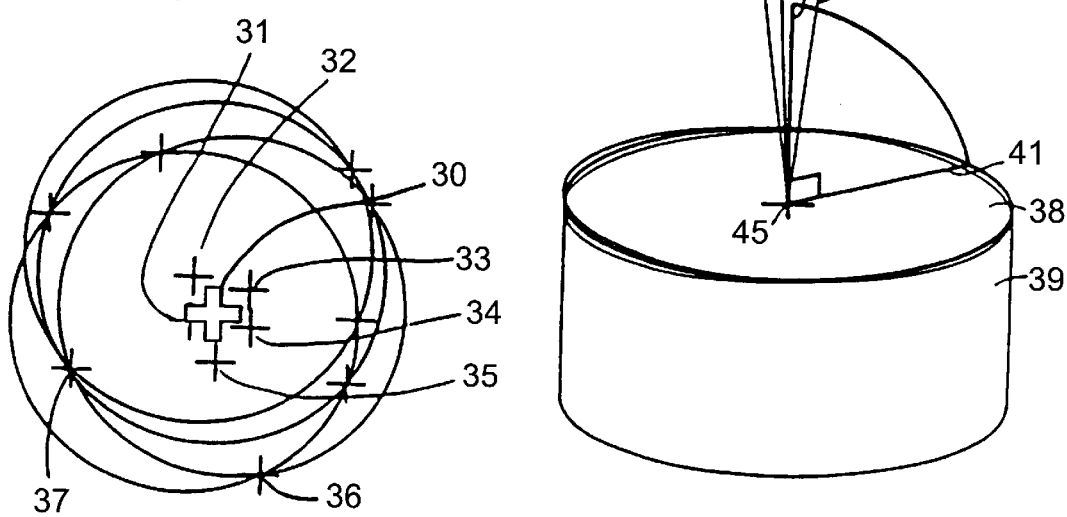
Fig. 3
Fig. 4

METHOD AND ARRANGEMENT FOR COLLECTING DATA FOR PRODUCTION OF REPLACEMENT DENTAL PARTS FOR THE HUMAN BODY

TECHNICAL FIELD

The present invention relates to a method for collecting control data or manufacturing data: for example, data on cutting coordinates for one or more machines or manufacturing systems; for production of artificial support members; or replacement parts for the human body. The members and parts preferably include dental bridges, dental caps, or other dental articles to be placed in the mouth cavity. The method utilizes stereophotography in which each imaging is carried out from different angles in relation to the relevant body areas, for example the jaw, teeth, etc., which are to be provided with the support members or replacement parts. The present invention also relates to an arrangement for implementing the method. The data collected can also be used for blasting fungi in the mouth cavity.

BACKGROUND OF THE INVENTION

It is already known to provide devices and methods for collecting control data, in which a model is produced and is scanned by reading equipment, and in which the shape of the model can be represented by, or with, digitized data which is processed or used in computer equipment for production of the manufacturing data.

It is also known to use equipment for stereophotography of, for example, the mouth cavity of a patient, the photographs being used for determining the positions of the implant and the like in the mouth cavity. The determination of the positions of the implant can in this case be carried out photogrammetrically.

DESCRIPTION OF THE INVENTION

TECHNICAL PROBLEM

The use of models entails relatively complicated and time-consuming procedures for the designing and production of implants and artificial support members for dental bridges, dental caps, etc. The model is produced by, among other things, taking an impression in the patient's mouth. Many patients cannot tolerate, or are averse to is such impression techniques. There is therefore, a need for simplified methods and arrangements, for example, in the production of dental bridges. The invention is directed to solving this problem.

The use of models, in itself, results in relatively large sources of error in the finished constructions which, on account of inadequate fitting, build static stresses into the patient's mouth and which, in the long term, cause the collapse of parts of the jaw bone despite the fact that the stresses are relatively small. The invention aims to solve this problem too, and it proposes a method and device which make it possible to eliminate built-in forces of this kind.

The use of stereophotography and photogrammetry for establishing the positions of teeth and implants in the mouth cavity should in itself be able to obviate the use of models which are produced using an impression compound in the patient's mouth. However, equipment used hitherto for stereophotography has proved to be impractical when employed in connection with dental work in the mouth cavity. Stereophotography involves imaging the same jaw area or implant/object from different angles, and this means that it has hitherto been proposed to use several cameras which have been coordinated in terms of their function. The equipment becomes complex, and it is difficult to prevent the movements the patient makes between the exposures from affecting the result. The invention solves this problem too.

Computer equipment for production of dental articles is beginning to be introduced to an ever greater extent on the dental market. It is important to use computer equipment (personal computers) having easy-to-follow instructions so that the equipment can be used by persons who are not computer experts. The invention solves this problem too. This applies also to the proposed camera equipment which, according to the invention, is calibrated for high-quality use in connection with manufacturing and has a user-friendly construction. It is important that the camera equipment be of a conventional type and does not require the use of advanced photography techniques for taking pictures. The invention solves this problem too.

Identification of the end surfaces by means of software in the computer equipment must not, by itself, involve a complicated management of the computer equipment. The invention solves this problem and proposes an embodiment in which standard software sold on the market will be used for the identification.

SUMMARY OF THE INVENTION

The characterizing feature of the present invention is, among other things, that the respective body area in question is stereophotographed using a single camera arranged to take simultaneous pictures of the body area or body areas from different angles at one and the same exposure. The different pictures taken simultaneously in this way are developed and are read by reading equipment which, as a function of the reading, generates digitized data concerning the stereophotographed body area and/or the object or objects which is or are applied in this area such as an implant or implants. The digitized data is transmitted to computer equipment in which the digitized data is processed or used to permit graphic reproduction on the screen of the computer equipment, or on another screen of another medium. Surfaces, for example end surfaces, of the body area in question (a tooth remnant, or example) and/or of the object applied on this area are then identified, which object, in accordance with the above, can be an implant. The identification takes place until the data, collected by the computer equipment, concerning the surfaces thus identified is used as control or manufacturing data. Alternatively, the data can be integrated in the control or manufacturing data together with other function data. This function data can relate, for example, to the available space for the respective support member or replacement part. The function data can also relate to aesthetic requirements placed on the respective support member or replacement part in this context. In one embodiment of the inventive concept, the mucous membrane of the mouth cavity is imaged (photographed) for reproducing the topography of the mucous membrane. The imaging is carried out in conjunction with, or prior to the production and can, for example, be taken as a basis for the treatment of the patient. The collection of data can also be used in the blasting of fungi in the mouth cavity.

The feature which characterizes an arrangement according to the present is that the camera equipment comprises a single camera which is arranged to take simultaneous pictures of the respective body area or body areas from different angles during one exposure. Also included is reading equipment, which is arranged to scan pictures taken simultaneously with the camera and to output, as a function of the scanning, digitized data concerning the structure or shape of the body area or body areas and/or of the object or objects applied in this area or these areas, such as implants. The computer equipment is arranged to receive and to process or use the digitized data for graphic reproduction, on the screen of the computer equipment, of the structure/structures or shape/shapes of the respective area and/or object. The computer equipment is arranged to identify, with the aid of identification software, the position or positions in space of one or more surfaces, for example end surfaces, of the respective area (tooth remnant, for example) and/or of an object applied on this area, for example the implant. In addition, means are provided for generating the manufacturing data using the data relating to the identified surfaces, if appropriate, together with function data on the available space for, and/or aesthetic requirements of, the respective support member or part, etc.

In one embodiment of the inventive concept, the identification software is arranged to operate with reference markings applied on the said surfaces. These markings preferably consist of circles or have designs of a corresponding geometrical nature. The software performs the identification by, among other things, comparing the simultaneously taken pictures of the respective area(s) and/or objects with the reference markings which are applied or present thereon. Any difference in the comparison can be observed in the geographical reproduction. One or more compensating actions or compensating measures for eliminating the difference in the graphic reproduction can be carried out on the computer equipment. When a difference in the correspondence between the pictures and the reference markings has been at least substantially eliminated, the program creates data on the actual position of the surface in question, which position can be represented by the position of the center point of the surface, of the inclination of the surface in space, etc. A unit which can be applied on the respective area, tooth remnant, implant, etc. is provided with reference markings in the form of circles about the periphery or circumference of the top surface of the unit. The identification program identifies points in images in the coordinate system of the picture. Data obtained is input for a photogrammetric calculation of image coordinates in accordance with a known process.

In one embodiment, the said camera is arranged to take pictures in or at the mouth cavity at a distance of 50 to 150 mm. The imaging can involve stereophotography of implants in the jaw, either at the level of the fixture, i.e. down in the jaw in the unhealed state of the latter, or at the level of the spacer, where the jaw is healed and only the spacers on the implant protrude above the healed jaw bone. The center points and inclinations of the end surfaces can be determined in this way, and the values determined are used for a dental bridge construction, a dental cap construction, or the construction of another dental article. The camera in question can operate with two virtual lens functions arranged at a distance from one another for achieving the stereo effect. The camera can thus effect three images of the respective area or areas and/or object. Two or more images are thus used, which include the images effected with the virtual lens functions. For determining the inclination of the surface, use is made of a surface normal in the form of a three-dimensional vector with a length which essentially corresponds to the length of the radius of the end surface (or equivalent).

The imaging can involve stereophotography of a number of implants, for example 2 to 6 implants. Each implant has in this case essentially the shape of a cylinder, the end surface of which is to be identified in space. Adaptations by building the respective implant up to a common level in a dental bridge can be carried out using calculations in the computer equipment. The precision of the determination of the solid angle for the implant or the abutment surface of the cylinder, which abutment surface is formed by the end surface, is of the order of magnitude of 0.01 radians, which corresponds to an error of of about 0.03 mm at the periphery of the implant/cylinder. The precision of the determination of an individual point on the respective area and/or the implant/cylinder, for example center points in the end surface, is about 0.02 mm.

BRIEF DESCRIPTION OF DRAWINGS

A presently proposed embodiment of a method and arrangement according to the invention will be described hereinbelow with reference to the attached drawings, in which:

FIG. 2 shows, in a basic diagram form, a radiation pattern for a camera which is used with mirror surfaces for achieving virtual lens functions with which stereophotography can be performed, FIG. 3 shows, from above, end surfaces which have been taken by stereophotography with the camera according to FIG. 2, and have been reproduced graphically on a computer screen, FIG. 4 shows, seen in a perspective view obliquely from above, the inclination of an implant and its end surface.

DESCRIPTION OF A PREFERRED EMBODIMENT(S)

Figure 1:
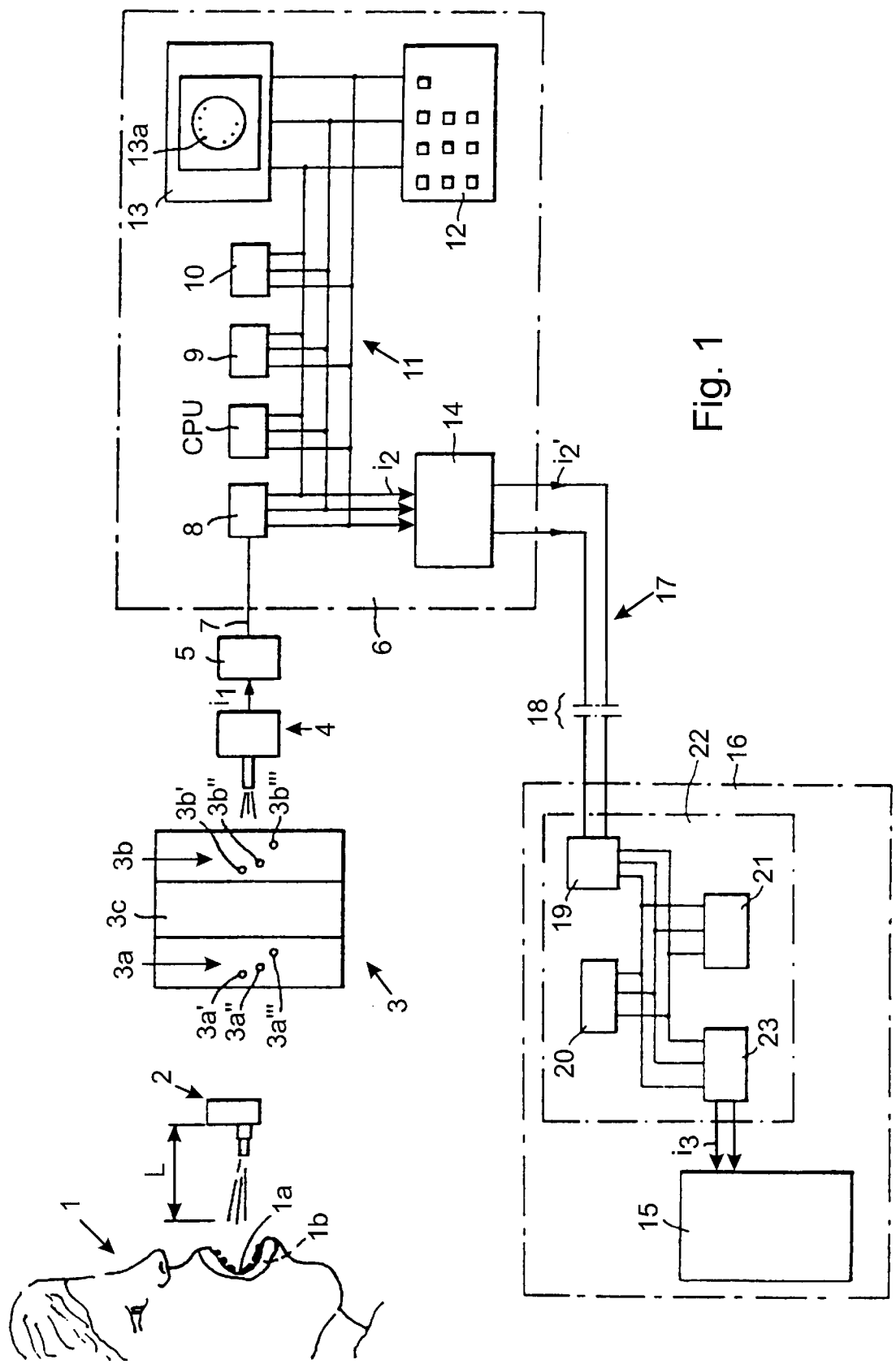
FIG. 1 shows in an outline, and in a block diagram form, the chain of steps involved in the production of a dental article for the human body.

A patient is indicated by 1 in FIG. 1. Stereophotography with a camera 2 is performed directly on the patient, in his or her mouth cavity 1a. The photography can involve photography of implants which have been implanted into the jaw bone 1b of the patient. The camera is of such a type that stereophotography can take place with a single exposure in accordance with what is described below. The camera is a miniature camera and is described in more detail in the Swedish patent application [lacuna] filed on the same day. The picture is taken at a distance L of about 50 to 150 mm. Reference number 3 shows a photograph which has been taken with the camera 2. The photograph presents two images 3a, 3b of the same object, but taken from different angles. A third image, which can be present in the zone 3c, is not used in the present case.

The photograph can be divided into several zones, each one of which presents its own image of the object in question, which object can be a jaw bone part, one or more implants, etc. In the present case, the spatial position of an implant is to be identified. In this case, use is made of the end surface of the implant, and of reference markings applied on this end surface, with three reference markings on such a surface having been shown on each image in the respective zone by 3a', 3a'', 3a''' and 3b', 3b'', 3b''' respectively. The images on the photograph 3 are scanned with a reading device 4 of a type known. The reading device can thus consist of the KODAK photo CD system, Hasselblad's slide scanner, etc. The reading device is, in this case, arranged to represent, with digital signals $i_1$, the shape in question which has been read, in the present case attributable to, among other things, the reference markings. The digitized data is stored in a storage unit 5 and can be transmitted to computer equipment 6. The transmission can be by wire 7, via diskette, without wires, etc. The data $i_1$ in question is received in the computer equipment in an adaptor unit 8. The computer equipment comprises a microprocessor (CPU), memory elements 9, 10, a bus connection 11 through which all the units of the computer equipment are connected to each other, a terminal 12 and a computer screen 13. Also included is a readout unit 14.

The data $i_1$ is received and processed or used in the computer equipment 6 to be able to reproduce graphically, on the screen 13, the body area, the object 13a, etc. which has been photographed and which is imaged on the photograph 3. The computer operates with a graphics program which is known. The computer similarly operates with an identification program, which is known for identifying the shape, spatial position, etc. of the area or the object which has been imaged. An example which may be mentioned of a graphics program is "NIH Image" from the National Institute of Health, USA. As an example of an identification program, the last-mentioned program can be used, or "Photo 3D" from Harry W. Townes, Montana, USA. Computation software which can be used is "CAP, $K^2$-konsultanse", Germany. The computer equipment is operated via the terminal 12 in a known manner.

Following identification of shape, position, etc., the identification data $i_2$ in question is read out to the readout element 14, which, in turn, transmits control data or manufacturing data $i_2'$ to one or more manufacturing machines 15, or to one or more manufacturing systems 16 which include the machine/machines. The transmission is effected by wire 17, without wires, via diskette, etc. In the case of wire/wireless transmission, the transmission can be effected via the public telephone network 18. The manufacturing system can include an adaptor unit 19, computer element 20 (CPU), memory and terminal element 21, which can also include a screen in the same way as the computer equipment 6. In FIG. 1, the second computer equipment is indicated by 22. In this case, too there is a readout unit 23, from which cutting coordinate data and other manufacturing data $i_3$ are transmitted to the machine(s).

FIG. 2 shows parts of the function of the camera. The camera has an actual or real lens 24. The imaging surface is indicated by 25, and the camera is provided with two parallel mirror surfaces or reflection surfaces 26, 27. The mirror surfaces or reflection surfaces are arranged in such a way that two virtual lens functions 28, 29 are created. The virtual lens functions are situated at a distance L' from each other and three images or image zones (cf. 3a, 3b and 3c in FIG. 1) are obtained on the imaging surface 25. Each of the two virtual lens functions 28, 29 gives its own image zone and its own image, while the real lens 24 gives an image or image zone pertaining to itself. Imaging of one and the same body area/body areas or object (implant, cap, dental bridge, etc.) is thus obtained through the distance L'.

With the arrangement according to FIG. 2, it is possible, by using more mirrors, to obtain more than two image zones, for example, four image zones, and consequently four different images. The images are compared in the computer equipment 6 with the aid of the identification program. According to FIG. 3, four different images are compared. A mean value 30 defines a number of center points 31, 32, 33, 34 and 35 for possible circles through 3 of peripheral points, of which two have been shown by 36 and 37.

In a similar way, the angle of inclination for the body in question can be worked out by calculating the solid angle. FIG. 4 shows an end surface 38 of an object 39. A three-dimensional vector is shown by 40, and a radius by 41. Different axes of inclination which are used in the calculation are shown by 42, 43 and 44. A center point is indicated by 45.

Figure 5:
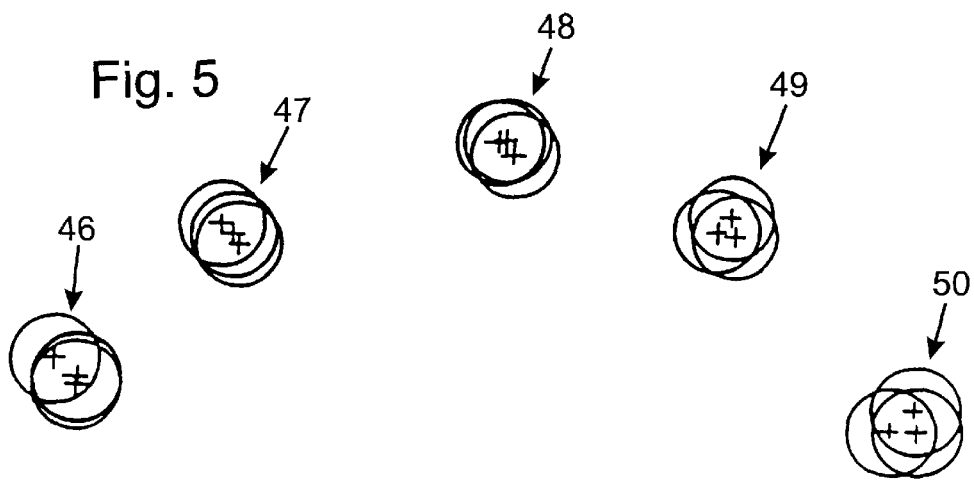
FIG. 5 shows, from above, the end surfaces of a number of implants which have been taken by stereophotography and have been reproduced graphically on a computer screen.

FIG. 5 shows the images of five different implants 46, 47, 48, 49 and 50. The center points and angles of inclination of these implants are estimated in accordance with the above. By means of the fact that the inclinations and the positions of the center points have been determined in this way, control data (see $i_2'$ in FIG. 1) can be extracted. The precision of the determination of the center points and of the angles of inclination is, in this case, extremely high, and reference is made to the precisions mentioned above.

Figure 6:
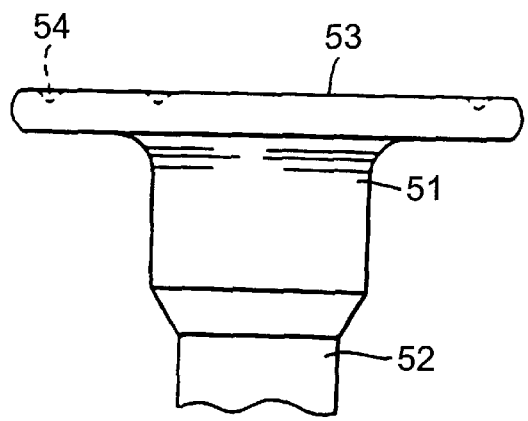
FIG. 6 shows, from the side, a unit which has been placed on an implant and which is provided with circular reference markings on its top surface, about its periphery.
Figure 7:
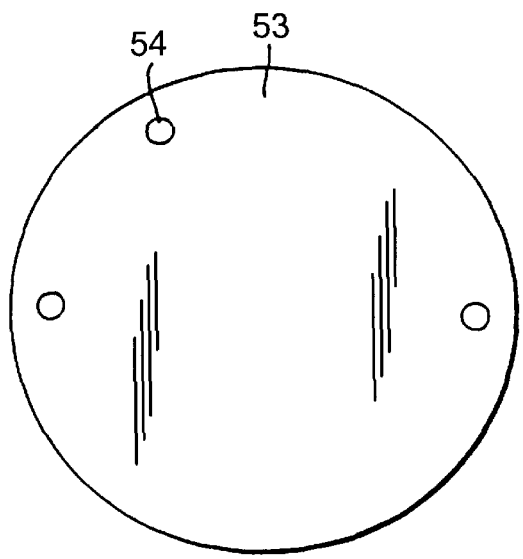
FIG. 7 shows, in a top view, the unit according to FIG. 6.

FIG. 6 shows a unit 51. The unit can be fixed on an implant 52 or other object. The unit is provided on its top surface 53 with peripheral, circular reference markings. The, positioning and the shape of these reference markings are shown in FIG. 7. The identification program used in the computer 6 can, in this case, be made to operate with the aid of the circular reference markings. In accordance with the above, image coordinate data is collected and is used in the calculation of the spatial coordinates, which calculation can be done in a known manner using the photogrammetric computation program.

The invention is not limited to the embodiment shown hereinabove by way of example, but instead can be modified within the scope of the attached patent claims and the inventive concept.

We claim:

1. An apparatus for collecting control data for production of replacement dental parts for the human body comprising:
   (a) means for imaging at least one of a body area and replacement part with a single imaging device arranged to take simultaneous pictures of the body area from different angles during one exposure;
   (b) means for developing the pictures and scanning them with a reading device;
   (c) means for generating digitized data of at least one of the imaged body area and replacement part to be applied in the area from the reading device;
   (d) means for transmitting the digitized data to computer equipment which automatically reproduces the body area and replacement part;
   (e) means for calculating spacial relations data of surfaces of at least one of the body area and replacement part with a photogrammetric computer program; and
   (f) means for using above data as control data in making and fitting the replacement part.

2. The apparatus of claim 1 wherein the means for imaging comprises a camera arranged to take pictures of the mouth cavity at a distance of about 50 to 150 mm, at one of the level of a fixture, down in the jaw, in an unhealed state and at the level of a spacer, in a healed state, with only spacers protruding above the healed jaw bone.

3. The apparatus of claim 2 wherein the camera comprises at least two virtual lens arranged at a predetermined distance from each other whereby a reduced number of pictures with actual lens functions are used to determine to position of body areas.

4. A method for collecting control data for production of replacement dental parts for the human body comprising the steps of:

(a) imaging at least one of a body area and replacement part with a single imaging device arranged to take simultaneous pictures of the body area from different angles during one exposure;

(b) developing the pictures and scanning them with a reading device;

(c) generating digitized data of at least one of the imaged body area and replacement part to be applied in the area from the reading device;

(d) transmitting the digitized data to computer equipment which automatically reproduces the body area and replacement part;

(e) calculating spacial relations data of surfaces of at least one of the body area and replacement part with a photogrammetric computer program; and (f) using above data as control data in making and fitting the replacement part.

5. The method of claim 4 wherein the body area comprises mucous membrane in the mouth cavity whereby topography of the mucous membrane is reproduced.

6. The method of claim 4 further comprising the steps of, placing reference markings on at least one of the body area and replacement part; and comparing the simultaneous pictures with respect to the reference markings to identify surfaces of at least one of the body area and replacement part.

7. The method of claim 6 wherein the reference markings have substantially circular shapes.

8. The method of claim 6 further comprising the step of placing no more than three reference markings around the periphery of at least one of the body area and replacement part to determine the center of the body area and replacement part.

9. The method of claim 4 wherein step (e) further comprises determining an inclination of at least one of the body are and replacement part with a surface normal in the form of a three-dimensional vector whose length substantial corresponds to a length of a radius of the body area and replacement part.

10. The method of claim 4 wherein step (e) further comprises determining a solid angle for an end of at least one of the body area and replacement part, said solid angle is determined with a precision of an order of magnitude of 0.01 radians.

11. The method of claim 4 wherein step (e) further comprises determining the position of individual points on at least one of the body area and replacement part, the precision of determining a point on the body area and replacement part is of the order of magnitude of 0.02 mm.

* * * * *

UNITED STATES PATENT AND TRADEMARK OFFICE
CERTIFICATE OF CORRECTION

PATENT NO. : 5,851,115
DATED : December 22, 1998
INVENTOR(S) : Carlsson et al.

It is certified that error appears in the above-identified patent and that said Letters Patent is hereby corrected as shown below:

On the title page, please insert :

item [73] Assignee: change "Gohenborg" to --Göteborg--.

Signed and Sealed this

Eleventh Day of May, 1999

Attest:

Q. TODD DICKINSON

Attesting Officer     Acting Commissioner of Patents and Trademarks